United States Patent
Tang et al.

(10) Patent No.: US 9,859,087 B2
(45) Date of Patent: Jan. 2, 2018

(54) X-RAY GENERATING APPARATUS AND X-RAY FLUOROSCOPYIMAGING SYSTEM EQUIPPED WITH THE SAME

(71) Applicants: NUCTECH COMPANY LIMITED, Beijing (CN); TSINGHUA UNIVERSITY, Beijing (CN)

(72) Inventors: Huaping Tang, Beijing (CN); Chuanxiang Tang, Beijing (CN); Huaibi Chen, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 198 days.

(21) Appl. No.: 14/582,060

(22) Filed: Dec. 23, 2014

(65) Prior Publication Data

US 2015/0187535 A1    Jul. 2, 2015

(30) Foreign Application Priority Data

Dec. 30, 2013  (CN) .......................... 2013 1 0741400

(51) Int. Cl.
H01J 5/18       (2006.01)
H01J 35/14      (2006.01)
(Continued)

(52) U.S. Cl.
CPC ............ *H01J 35/14* (2013.01); *G01N 23/043* (2013.01); *G21K 1/02* (2013.01); *H01J 35/16* (2013.01); *H01J 2235/166* (2013.01)

(58) Field of Classification Search
CPC ............... H01L 21/187; H01L 27/0921; H01L 29/1087; H01L 21/263; H01L 21/18;
(Continued)

(56) References Cited

U.S. PATENT DOCUMENTS

| 1,714,975 | A | | 5/1929 | Coolidge | |
|---|---|---|---|---|---|
| 4,020,356 | A | * | 4/1977 | Brahme | A61N 5/10 250/492.1 |
| 4,731,807 | A | * | 3/1988 | Plessis | A61B 6/032 378/146 |
| 6,282,263 | B1 | * | 8/2001 | Arndt | H01J 35/14 378/113 |

(Continued)

FOREIGN PATENT DOCUMENTS

JP   H06188092 A    7/1994
WO   2004/010162 A2  1/2004

OTHER PUBLICATIONS

The extended European Search Report issued in the corresponding EP application dated May 12, 2015.

(Continued)

*Primary Examiner* — Irakli Kiknadze
(74) *Attorney, Agent, or Firm* — Kilpatrick Townsend & Stockton LLP

(57) ABSTRACT

The present invention provides an X-ray generating apparatus and an X-ray fluoroscopy imaging system comprising the same. The X-ray generating apparatus comprises: an electron accelerator including an electron acceleration unit, an electron emission unit, and a target; a shielding and collimating device, including a shielding structure and a collimator arranged in the shielding structure, wherein the target is surrounded by the shielding structure, the collimator is arranged in a direction passing through the target point and forming an angle from 30 degrees to 150 degrees with the electron beam shooting the target.

9 Claims, 4 Drawing Sheets

(51) Int. Cl.
*G01N 23/04* (2006.01)
*G21K 1/02* (2006.01)
*H01J 35/16* (2006.01)

(58) Field of Classification Search
CPC .............. H01L 21/182; H01L 21/185; H01L 29/66136; H01L 29/78; H01L 29/868; H01L 21/02013; H01L 21/304; H01L 21/6835; H01L 27/092; G01N 23/06; G01N 2223/419; G01N 23/046; G01N 23/043; G01N 2223/402; G01N 2223/626; G01N 2223/639; G01N 23/04; G01V 5/0008; G01V 5/005; G01V 5/0016; G06K 19/0701; G06K 19/0723; H03K 17/223; H03K 2217/0018; G21K 1/02; H01J 2235/166; H01J 35/14; H01J 35/16; H01J 2235/087; H01J 35/18; H01J 35/08; H01J 2235/168; H01J 2235/186; H01J 35/06; H01J 2235/122; H01J 2235/086; H01J 2235/18; H01J 35/12; H01J 5/18; H01J 2235/06; H01J 2235/183; H01J 2235/081
USPC .................. 378/4, 19, 57, 119, 145, 140
See application file for complete search history.

(56) References Cited

U.S. PATENT DOCUMENTS

| | | | |
|---|---|---|---|
| 6,366,021 | B1 | 4/2002 | Meddaugh et al. |
| 7,436,934 | B2* | 10/2008 | Hartick .................. G21K 1/04 378/149 |
| 7,573,975 | B2* | 8/2009 | Xu .......................... A61B 6/06 378/149 |
| 2004/0057554 | A1* | 3/2004 | Bjorkholm ........... G01V 5/0016 378/143 |
| 2006/0023835 | A1* | 2/2006 | Seppi ..................... G01N 23/046 378/57 |
| 2007/0092062 | A1* | 4/2007 | Reynolds ................. H05H 7/00 378/121 |
| 2008/0205590 | A1* | 8/2008 | Xie ...................... G01V 5/0058 378/41 |

OTHER PUBLICATIONS

The first Office Action dated Aug. 3, 2016 in the corresponding European Application No. 14200018.1.
The second Office Action dated Jun. 28, 2017 in the corresponding European Application No. 14200018.1.

* cited by examiner (A)

(B)

(C)

X-RAY GENERATING APPARATUS AND X-RAY FLUOROSCOPYIMAGING SYSTEM EQUIPPED WITH THE SAME

This application claims priority to Chinese Patent Application No. 201310741400.3, filed on Dec. 30, 2013, which is hereby incorporated by reference in its entirety.

FIELD OF THE INVENTION

The present invention relates to an apparatus for generating an X-ray beam, and more specifically, to an apparatus for generating a planar fan-shaped high energy X-ray beam having a uniform intensity distribution using a high energy electron accelerator.

BACKGROUND OF THE INVENTION

X-rays radiation has wide applications in industry non-destructive testing, security inspection and other domains. For large objects to be tested, e.g., boilers, airspace engines, mass cargoes at airports/railway stations/customs, high energy X-rays are required for their fluoroscopy examinations, generally produced by electron accelerators at energies above 2 MeV. The basic way of producing X-rays by an electron accelerator is as follows: producing an electron beam with an electron gun, accelerating the electron beam by an electric field to obtain high energy, shooting a target by the high energy electron beam to produce X-rays. X-rays produced by the electron beam shooting on the target generally distribute in various direction at a 4π solid angle. X-rays produced by electron beams with different energies shooting on a target may have different intensity distributions in various radiation directions. In general, the higher energy an electron beam has, the higher intensity the forward X-rays have, and the lower intensity the X-rays in the other directions have. With a target point as the center and X-ray intensity in various directions as amplitude, the X-ray intensity has a "pine core shaped" distribution over solid angles as shown in FIG. 3. In various X-ray fluoroscopy imaging systems, instead of adopting all X-rays over the 4π solid angle, only a small portion is adopted. In many situations, X-rays in a planar fan-shaped area are used, such as a sliced "planar fan-shaped beam". As shown in FIG. 2, such a system is composed by a high energy electron accelerator, a shielding and collimating device, a detector and a signal analysis and image processing system, with dotted arrows schematically showing a "planar fan-shaped beam". "Planar fan-shaped beams" have wide applications in high energy industry CT, container inspection systems, vehicle inspection systems, train fluoroscopy examination systems, air cargo inspection systems, luggage and parcel inspection systems and the like.

In existing methods for obtaining a "planar fan-shaped beam" in the prior art, a "thin gap" shielding collimator is arranged in front of the target of the high energy electron accelerator to shield X-rays in most of directions while only passing X-rays through the "thin gap" to form a "planar fan-shaped beam". In general, the "thin gap" is arranged directly in front of the target, and on the advancing direction of the shooting electron beam, which is referred to as "zero degree" direction herein. The highest intensity of X-rays produced by electron accelerators is used in the prior art. However, there are large differences between X-ray intensities in different directions in the fan area. Taking a 9 MeV accelerator as an example, the X-ray intensity in the zero degree direction of the fan area is 10 times of that in the 45-degree direction at the edge. After many years of development of the X-ray fluoroscopy imaging system shown in FIG. 2, there is a great improvement on the performance of the detector, and the demand for the intensity of X-rays has been significantly reduced. However, in order to improve image quality, there is an increasing requirement for the quality of X-rays. For example, a ratio of intensity differences of X-rays in various directions in the fan area, of less than 2, i.e., a "planar fan-shaped beam having uniform intensity", is desired.

SUMMARY OF THE INVENTION

The present invention has been proposed to solve one of the above problems. An object of the present invention is to provide an apparatus for generating a high energy planar fan-shaped X-ray beam having uniform intensity to meet the requirement of the development of X-ray fluoroscopy imaging system technologies.

The present invention provides an X-ray generating apparatus, characterized in comprising:

a high energy electron accelerator including an electron acceleration unit, an electron emission unit mounted on one end of the electron acceleration unit, and a target mounted on the other end of the electron acceleration unit; and a shielding and collimating device, including a shielding structure and a collimator arranged in the shielding structure, wherein the target is surrounded by the shielding structure and is shot by an electron beam coming from the electron emission unit and accelerated by the electron acceleration unit to generate X-rays, the collimator is arranged in a direction forming an angle from 30 degrees to 150 degrees with the electron beam shooting the target and passing through the target point.

Said one end of the electron acceleration unit refers to the acceleration starting position of the electron acceleration unit, and the other end of the electron acceleration unit refers to the acceleration ending position of the electron acceleration unit.

Further, in the X-ray generating apparatus of the present invention, the electron accelerator has energy of above 2 MeV.

Further, in the X-ray generating apparatus of the present invention, the collimator is a planar fan-shaped gap arranged in the shielding structure.

Further, in the X-ray generating apparatus of the present invention, the electron accelerator further comprises an electron drift segment connected between the electron acceleration unit and the target.

Further, in the X-ray generating apparatus of the present invention, the electron drift segment is a small diameter conduit, wherein the small diameter conduit has an inner diameter larger than the diameter of the electron beam and an outer diameter less than the outer diameter of the electron acceleration unit.

Further, in the X-ray generating apparatus of the present invention, the shielding structure is made from a material that is able to block and absorb most of undesired X-rays; the target is a planer structure, a spherical surface structure or other curved surface structure.

Further, in the X-ray generating apparatus of the present invention, the shielding and collimating device has multiple collimators, the positions of which are symmetrical with respect to a plane passing the target point and perpendicular to the electron beam or are symmetrical with respect to the electron beam.

The present invention provides an X-ray fluoroscopy imaging system, characterized in comprising the X-ray generating apparatus described above.

The present invention mainly provides an apparatus for generating a high energy planar fan-shaped X-ray beam having uniform intensity. The apparatus for generating a high energy planar fan-shaped X-ray beam having uniform intensity of the present invention is composed of a high energy electron accelerator with an energy of above 2 MeV and a shielding and collimating device, wherein the collimator is arranged in a direction forming an angle in a range from 30 degrees to 150 degrees with the electron beam shooting the target, and the number of the collimators may be one or more than one.

In the present invention, by means of arranging the collimator in a direction forming a lager angle with the direction of the electron beam shooting the target, a X-ray beam may be obtained with better quality, such as (1) more uniform intensity of X-rays in various directions within a fan area on a plane; (2) smaller energy dispersion of X-rays within the fan area on the plane; and (3) a smaller size of target point with the projection point of X-rays on the plane being the target point. These three properties may improve the image quality of the X-ray fluoroscopy imaging system. Due to better uniformity of X-rays, X-rays may be drawn out at a large angle to increase X-ray coverage within a closer distance. Multiple collimators are arranged in the shielding and collimating device with different angle and position relationships, so as to realize: (1) obtaining multi-angles-of-views images from multiple angles of views; (2) obtaining double-energy effect by means of generating X-ray beams with different energy quantities from different collimators, so as to determine materials of objects under inspection; (3) implementing a double-channel inspection system using one accelerator to improve the inspection speed of the X-ray fluoroscopy imaging system and its cost performance; and a combination thereof to form a X-ray fluoroscopy imaging system in different combinations of double channel/high energy/multiple angles of views.

DETAILED DESCRIPTION OF THE EMBODIMENT

Below, the present invention will be described in detail with reference to the drawings.

Figure 1:
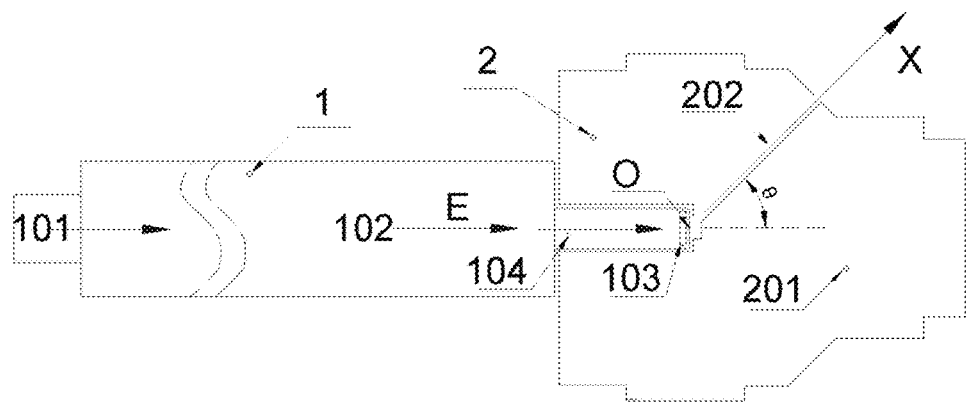
FIG. 1 is a schematic diagram of an X-ray generating apparatus of the present invention.
Figure 2:
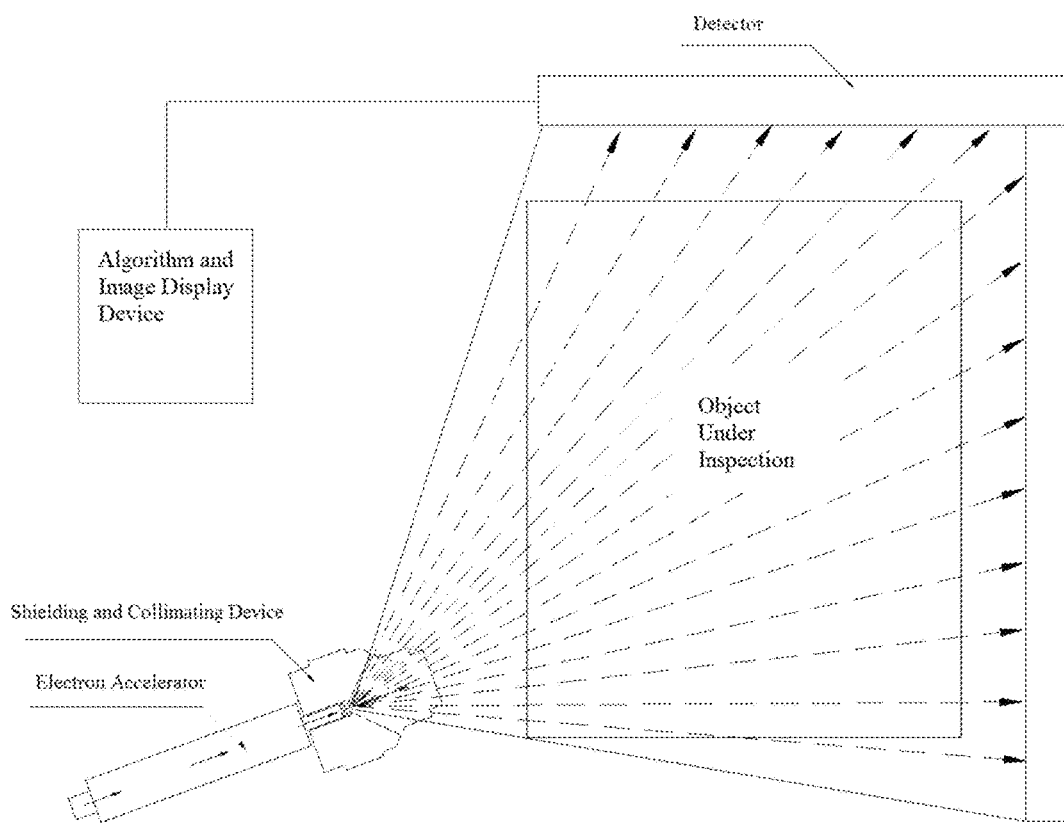
FIG. 2 is a schematic diagram of a planar fan-shaped high energy X-ray beam fluoroscopy imaging system.

FIG. 1 is a schematic diagram of an apparatus for generating a planar fan-shaped high energy X-ray beam having uniform intensity of the present invention. The apparatus for generating a planar fan-shaped high energy X-ray beam having uniform intensity of the present invention comprises high energy electron accelerator 1 and shielding and collimating device 2, wherein the high energy electron accelerator 1 comprises electron emission unit 101, electron acceleration unit 102 and target 103; the shielding and collimating device 2 comprises shielding structure 201 and collimators 202; the target 103 is surrounded by the shielding and collimating device 2, and the collimator 202 is arranged in a direction passing through the target point and forming an angle from 30 degrees to 150 degrees with an electron beam shooting the target.

Figure 3:
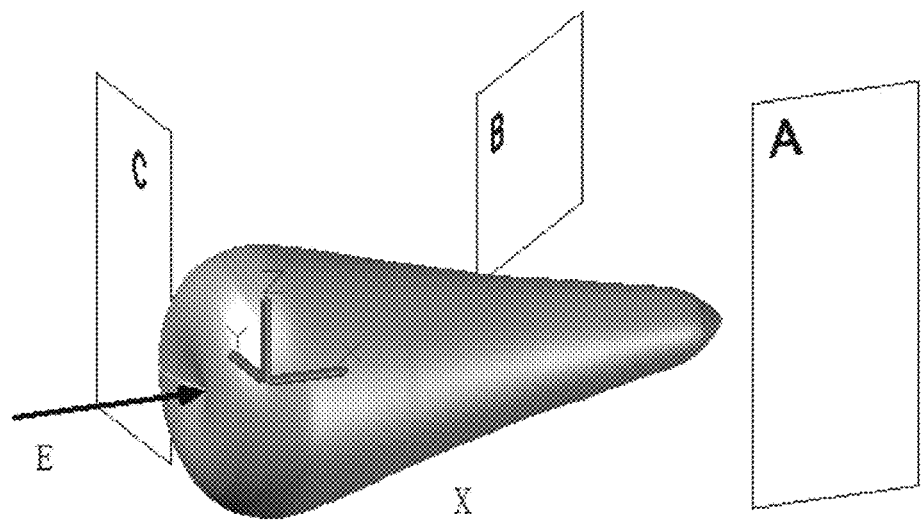
FIG. 3 is a schematic diagram of an intensity distribution of X-rays produced by a high energy electron accelerator at different angles (in a pine core shape)

Further, the electron accelerator 1 has energy of above 2 MeV (Million Electron Volt). The electron accelerator 1 is used to produce a high energy electron beam E, and in general comprises electron emission unit 101, electron acceleration unit 102 and target 103. The electron accelerators are widely used devices, including high voltage accelerators, induction accelerators, cyclotrons, linear accelerators, etc. The principle of the electron accelerators is as follows: with the operation of its power supply and control systems, the electron emission unit produces an initial electron beam E, which enters into the electron acceleration unit and is accelerated by a high voltage field, induction field, or microwave field to obtain high energy. The high energy electron beam E then bombards the target to produce X-rays in various directions with a $4\pi$ solid angle. In general, the moving direction of the electron beam E is defined as the forward direction. X-rays produced by the high energy electron beam E shooting the target have different intensity values in different directions, with a maximum value in the forward direction, and gradually reduced values as increasingly apart from the forward direction. The higher energy the electron beam has, the more apparent this variation becomes. For example, for X-rays produced by a 9 MeV electron beam shooting the target, if the intensity of central X-rays (in the forward direction) is defined as 100%, the radiation intensity is about 73% in a direction apart from the center direction by 5 degrees, about 53% in a direction apart by 10 degrees, about 40% in a direction apart by 15 degrees, about 18% in a direction apart by 30 degrees, about 10% in a direction apart by 45 degrees, about 7% in a direction apart by 60 degrees, about 5% in a direction apart by 90 degrees, and about 4% in a direction apart by 120 degrees, showing an apparent forward-direction centralized distribution. This distribution is axially symmetric with respect to the moving direction of the electron beam. With a position (referred to as a target point) shot by the electron beam as the center, FIG. 3 shows a graph of a 3D distribution of X-ray intensities at various angles on various directions within a $4\pi$ solid angle, just like a pine core and thus referred to as a "pine core shape". In FIG. 3, the electron beam E shoots the target to produce X-rays radiated in various directions at the target point. The X-rays have a 3D intensity distribution in a pine core shape. "X-Y-Z" are coordinate axes of the 3D distribution. A "X-Y" plane is defined as the horizontal plane, and other three planes A, B, C are observation planes perpendicular to the horizontal plane and forming different angles with the electron beam E.

Figure 4:
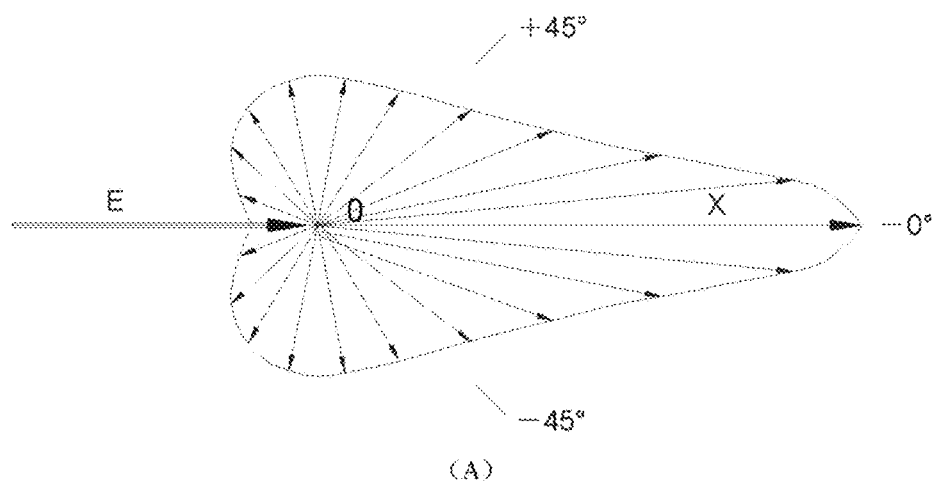
FIG. 4 shows planar X-ray beams obtained from collimators in different planes, (A) a X-ray beam on plane A; (B) a X-ray beam on plane B; (C) a X-ray beam on plane C.
Figure 4:
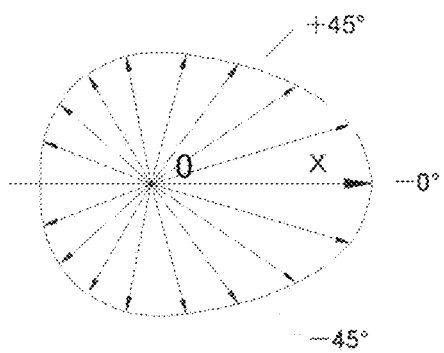
Figure 4:
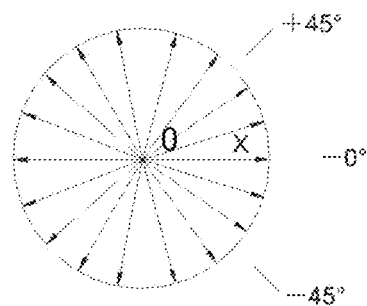

With the target point as the center and cutting the "pine core shape" with planes forming different angles with the shooting electron beam E, different sectional diagrams are obtained, showing 2D intensity distributions of X-rays on those planes at different angles, as shown in FIG. 4.

FIG. 4(A) shows an X-ray intensity distribution at different angles on plane A of FIG. 3. Since the plane A forms a zero degree angle with the electron beam E, the electron beam E may be observed on the plane A. The electron beam E shoots the target and produce X-rays radiated at various angles at the target point position o, wherein the X-ray intensity in the forward direction (the moving direction of the electron beam) has the maximum value, the larger angle a direction deviates from the zero degree direction, the smaller intensity the X-rays have in that direction. On the plane A, X-ray intensities in various directions have the largest difference in the distribution. For example, for a 9 MeV electron beam E, the X-ray intensity in the 0° direction is 10 times of that in the 45° direction and 20 times of that in the 90° direction.

FIG. 4 (B) shows an X-ray intensity distribution at different angles on plane B of FIG. 3. The plane B forms an angle between 0° to 90°, e.g., 45°, with the electron beam E. Although the electron beam E cannot be observed on this plane, still with the position o at which the electron beam E shoots the target as the center, X-rays produced by the electron beam E shooting the target radiate at various angles from the target point position o. Also, the intensity on the X-Y plane is the maximum, and is defined as a 0° direction. The larger angle a direction derives from the 0° direction on the plane B, the smaller intensity the X-rays have. However, because the largest X-ray intensity on the plane B is the intensity in a direction with an angle between the plane B and the electron beam E in the "pine core shaped" X-ray intensity distribution, for example, the intensity at the 45° direction, it is far less than that in the 0° direction on plane A. There are smaller differences between X-ray intensity distributions in various directions on the plane B.

FIG. 4 (C) shows an X-ray intensity distribution at different angles on plane C of FIG. 3. The plane C forms a 90° angle with the electron beam E. the shooting electron beam E is perpendicular to the plane C, still with the position o of shooting target as the center, X-rays produced by the electron beam E shooting the target radiate at various angles from the target point position. Intensities are consistent in various directions, equivalent to the intensity in the 90° direction in the "pine core shaped" distribution. There is not any difference between X-ray intensities in various directions on the plane C.

X-rays produced by an electron beam E shooting a target with energy E are in a continuous energy spectrum with energy from 0 to E. For X-rays having different energy quantities, their angle distribution complies with a certain rule, i.e., X-rays having higher energy are mostly distributed in the forward direction and in a range of smaller angles. The larger a direction derivates from the 0° direction, the lower average energy X-rays have in that direction. A detailed description about relevant characters of spectrum distribution may be found in technical documents of electron accelerator technology, high energy physics and so on. X-ray spectrum distributions obtained on observation planes other than planes A, B, C described above are similar to the intensity distributions shown in FIG. 4 (A), (B), (C), i.e., the higher intensity an angle corresponds to, the higher energy X-rays have at that angle.

The shielding and collimating device 2 comprises shielding structure 201 and collimators 202. The shielding structure 201 is made from a high Z material (i.e., high atomic number material), such as lead, tungsten, depleted uranium, for blocking and absorbing (i.e., shielding) most of undesired X-rays. X-rays comply with an exponential decay rule when passing through an object. The larger atomic number the object has or the higher density it has, the faster the X-rays decay. Thus, in general, the shielding structure 201 is made from a high Z material, such as a combination of one or more of lead, tungsten, and depleted uranium to block and absorb undesired X-rays. Because X-rays produced by a high energy electron beam shooting a target has a "pine core shaped" intensity distribution, the amounts of X-ray intensity to be blocked at different angles are different. So, the shielding structure has different thickness in different directions, generally like a "pine core shape". Commonly, for the simplicity of fabrication and saving material, the shielding structure 201 is an axisymmetric structure, with the moving direction of the shooting electron beam as its axis of symmetry, having thickness in various directions corresponding to the radiation intensity, and with a contour approximated by steps. Certainly, the shielding structure 201 may be in any other form, so long as the effect of shielding undesired X-rays may be produced and the requirement for the smallest thickness in various directions can be satisfied.

Figure 5:
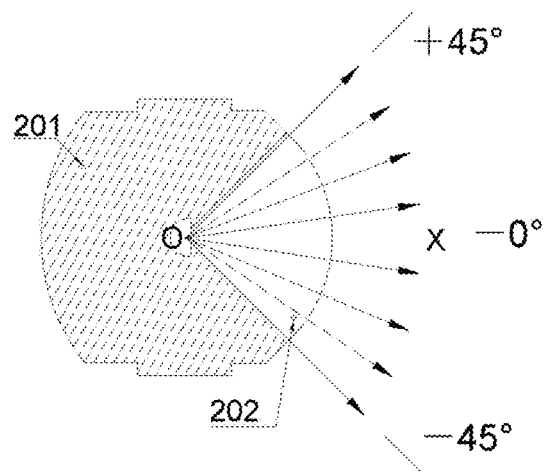
FIG. 5 is a schematic diagram of a sectional structure of the collimator on plane B shown in FIG. 4.

Further, the shielding and collimating device 2 comprises shielding structure 201 and collimators 202. The collimator 202 is a thin gap in a planar fan shape provided in the shielding structure 20 for drawing out X-rays to be used and confining the X-rays in a desired planar shape. The center of the fan is the target point o where the electron beam shoots the target. The thickness of the thin gap is in the order of millimeters, in general 0.5 mm to 5 mm, typically 2 mm, for example. Further, the thin gap may be a gap with a certain taper, for example, it may has a thinner thickness closer to the target point o and a thicker thickness apart from the target point o, for example, 1.5 mm at the target point, 2 mm at a middle portion, and 2.5 mm at the outlet of the gap. The collimator 202 confines the shape of the X-rays, comprising: defining the planar thickness of the X-rays by the thickness of the thin gap of the collimator 202; defining an emission angle range in the plane of the X-ray beam by the fan angle of the collimator 202, for example, 90°; defining the relative position of the center of the X-ray beam in the fan angle range by the position of the fan angle of the collimator 202 with respect to the "X-Y" horizontal plane, for example, the center of the X-ray beam is at 0°, the fan angle ranges from −30° to 60°, and totally opening angle of 90°. A sectional structure of the shielding and collimating device is shown in FIG. 5 is shown in FIG. 5, corresponding to a situation in which the collimator is located on plane B in FIG. 3 and the center is the target point o. The target point is surrounded by the solid shielding structure 201 to block and absorb undesired X-rays. The collimator 202 is a gap in a planar fan shape for drawing out X-rays to be used, and the fan has a center at 0° and has a 90° opening angle from −45° to +45°. Generally, for the convenience of processing, the shielding and collimating device 2 is divided into several parts for processing and then the processed parts are assembled. For example, the shielding and collimating device 2 is divided along the positions on the collimators 202, or is divided along the periphery of the collimators 202. Generally, the parts of the shielding structure 201 could be processed in a lower precision while the parts of the collimators 202 shall be processed in a higher precision and/or by using another material. Then, these parts are assembled into the shielding and collimating device 2. As a result, the shielding and collimating device 2 could be an integral structure, or it could be an assembled structure with multiple parts, for example, a structure in which the shielding structure is separate from the collimators.

In the present invention, the collimator 202 is characterized by forming an angle ranging from 30° to 150° between a plane where it locates and the electron beam E. As described above, in the prior art, the collimator is arranged directly in front of the target (at 0° or nearly 0°) to obtain a planar fan-shaped X-ray beam, as shown in plane A in FIG. 3, so that X-rays having the highest intensity and energy are located in the planar fan. However, with the development of existing technology, on one hand, it is very easy to realize a powerful X-ray beam using an industry high energy electron accelerator, for example, Hextron 3000 available from Nuctech Company Limited, under X-ray energy of 9 Mev, allowing a X-ray intensity of 3000 Rad/m·min at 0°, 540 Rad/m·min at 30°, and even 150 Rad/m·min at 90°, 120 Rad/m·min at 150°. On the other hand, the requirement for X-ray intensity in X-ray fluoroscopy imaging systems is constantly falling down. For example, in various types of products of large container inspection systems manufactured by the Nuctech Company Limited, only X-ray intensity of several or hundreds Rad/m·min is required. Thus, the intensity of planer fan-shaped X-ray beams obtained through arranging a collimator at a large angle such as plane B and plane C shown in FIG. 3 may completely meet the application requirement of existing products.

Through arranging collimators at large angles, planar fan-shaped X-ray beams obtained as such have better uniformity. As described above, as shown in FIG. 4, three collimators are arranged on planes A, B and C respectively to obtain X-ray beams, for all of which the "X-Y" horizontal plane is the 0° direction. In a fan area from −45° to +45° (90° in total), a planar fan-shaped X-ray beam obtained from the collimator on plane A has a central intensity that is 10 times of its edge intensity, a planar fan-shaped X-ray beam obtained from the collimator on plane B has a central intensity that is 2 times of its edge intensity, and a planar fan-shaped X-ray beam obtained from the collimator on plane C has a consistent intensity in various directions.

A planar fan-shaped X-ray beam obtained through arranging a collimator at a large angle has a spectrum character similar to its intensity character. In general, the larger angle between the plane where the collimator locates and the electron beam E, the lower average energy (or integrable energy) the X-ray beam has. Therefore, the X-ray spectrum character may be chosen deliberately through selecting the arrangement angle of the collimator.

Figure 6:
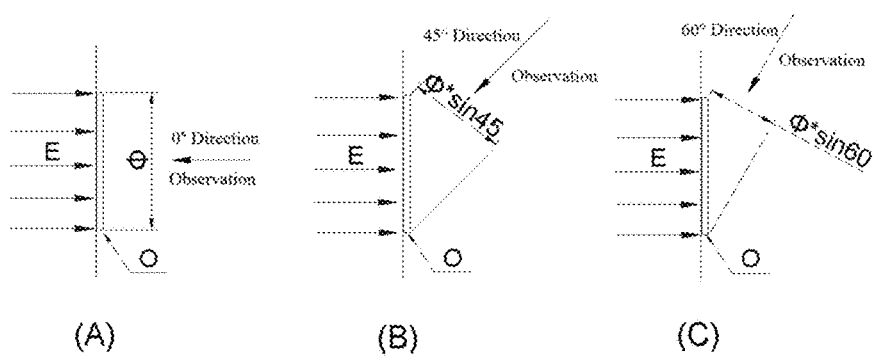
FIG. 6 is a schematic diagram of X-ray target point in different projection sizes when collimators are arranged on different planes.

For a planar fan-shaped X-ray beam obtained through arranging a collimator at a large angle, in terms of focus size of X-rays in the plane thickness direction, the projection has a smaller size. The electron beam E shoots the target and produces X-rays. The focus size of X-rays is the geometric distribution of the electron beam E, in general, a circle with a diameter $\Phi$. Planar fan-shaped X-ray beams obtained from collimators at different angles have different focus sizes in the plane thickness direction. As shown in FIG. 6, FIG. 6(A) shows that the X-ray focus size in the plane thickness direction is $\Phi$ when X-rays are drawn out from the collimator in the directly forward direction, which is equivalent to observing in the 0° direction. FIG. 6(B) shows that the X-ray focus size in the plane thickness direction is $\Phi*\sin 45°$, i.e., about $0.7\Phi$, when the X-rays are drawn out from the collimator in the 45° direction, which is equivalent to observing in the 45° direction. FIG. 6(C) shows that the X-ray focus size in the plane thickness direction is $\Phi*\sin 60°$, i.e., about $0.5\Phi$, when the X-rays are drawn out from the collimator in the 60° direction, which is equivalent to observing in the 60° direction. In a fluoroscopy imaging system using X-rays, the smaller the focus size is, the higher resolution an obtained image has. Thus arranging the collimator at a larger angle is helpful to reduce the focus size and thus improve image quality of the X-ray fluoroscopy imaging system.

Figure 7:
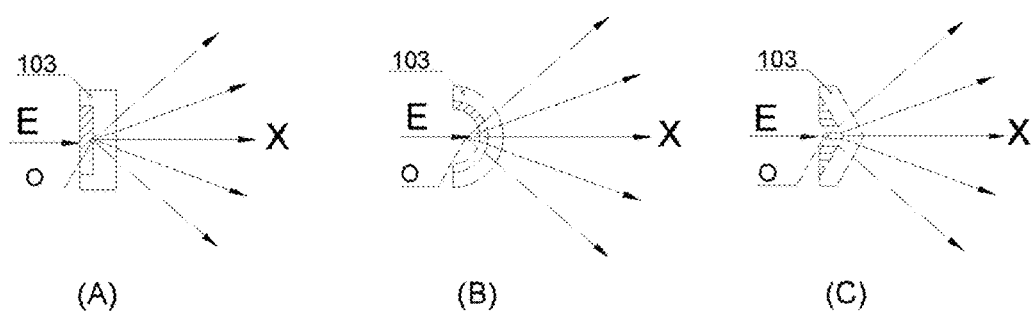
FIG. 7 is a schematic diagram of three target structures in different shapes, (A) planar target, (B) spherical surface target, and (C) L shaped target.

In the apparatus for generating a planar fan-shaped high energy X-ray beam having uniform intensity of the present invention, the target 103 may have a planar structure, a spherical surface structure, or other curved surface structure. As shown in FIG. 7, a structure schematic diagram of three targets in different shapes is shown. FIG. 7 (A) shows a planar target, FIG. 7 (B) shows a spherical surface target, and FIG. 7(C) shows an L-shaped target. Targets in different shapes may produce different effects in geometry on the focus of a planar fan-shaped X-ray beam drawn out from collimators arranged at different angles. It is advised in the present invention to flexibly select the target structure to adapt to different particular applications.

In the apparatus for generating a planar fan-shaped high energy X-ray beam having uniform intensity of the present invention, the high energy electron accelerator 1 further comprises electron drift segment 104 connecting the electron acceleration unit 102 and the target 103. The electron drift segment 104 is a small diameter conduit, wherein the electron drift segment 104 has an inner diameter larger than the diameter of the electron beam E and an outer diameter far less than the outer diameter of the electron acceleration unit 102. In the electron accelerator 1, the electron acceleration unit 102 generally has a larger size. When the target 103 is mounted at an end of the electron acceleration unit 102, on one hand, for shielding undesired side-back X-rays (larger than 90°) in the side-back direction, in order to guarantee that the shielding material has an enough thickness on its shielding path, the shielding structure 201 will have a larger size, causing higher cost; on the other hand, due to the blocking of the electron acceleration unit 102, it is difficult to draw out useful X-ray beams from the side-back direction for fluoroscopy imaging operation. Through arranging the electron drift segment 104 between the electron acceleration unit 102 and the target 103 to extend the target by a small diameter conduit, as shown in FIG. 1, on one hand, shielding may be easily realized with the reduced volume and cost of the shielding structure 201; on the other hand, it is allowed to draw out a planar fan-shaped X-ray beam from a direction larger than 90°.

Figure 8:
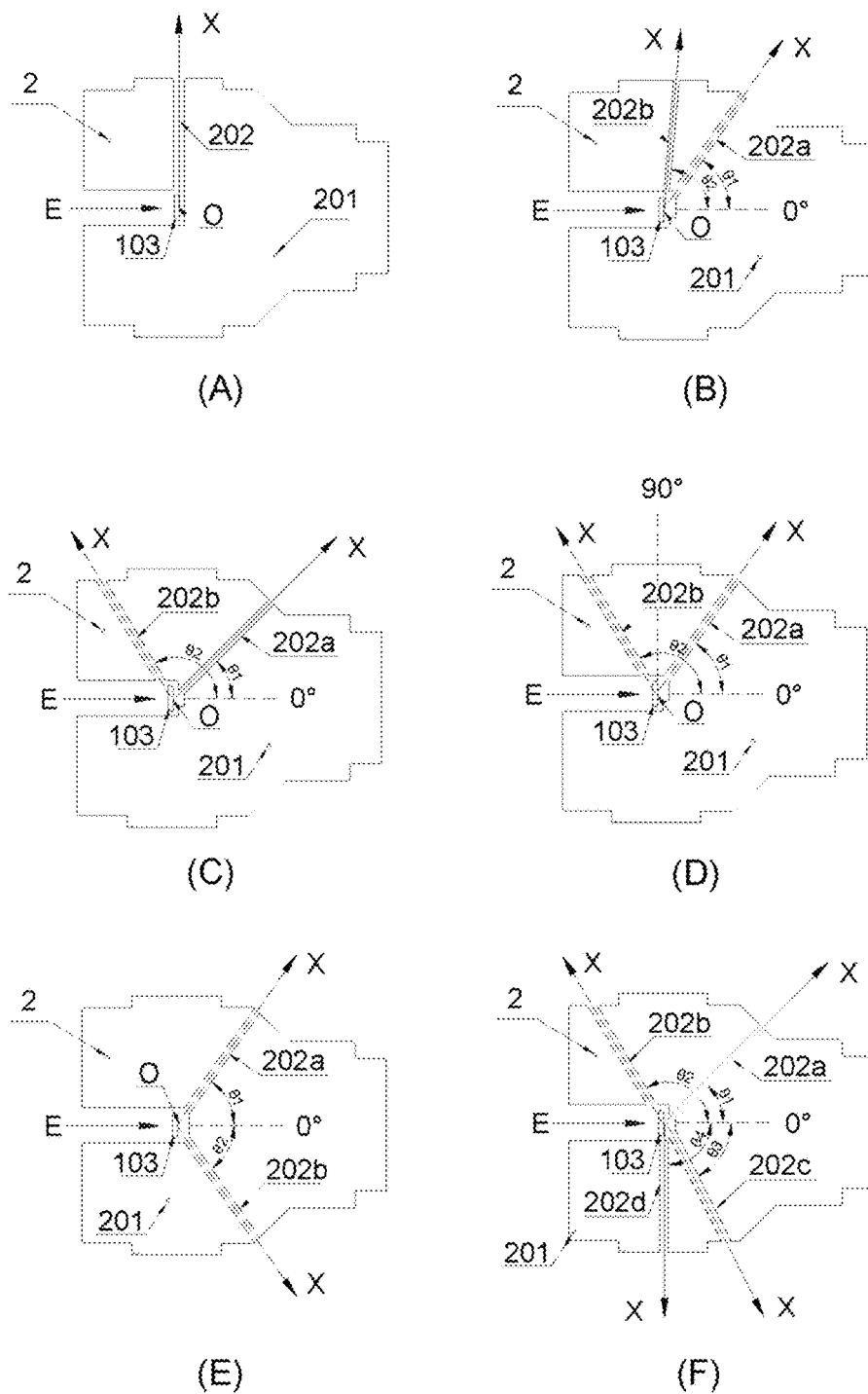
FIG. 8 is a schematic diagram of shielding and collimating devices with different structures.

In the apparatus for generating a planar fan-shaped high energy X-ray beam having uniform intensity of the present invention, there may be one or more collimators 202 arranged in a range from 30° to 150° to draw out one or more planar fan-shaped high energy X-ray beams having uniform intensity. FIG. 8 shows examples of arranging one or more collimators of the present invention.

FIG. 8 (A) shows an example of arranging a collimator in a direction forming nearly 90° with the electron beam E to draw out a planar fan-shaped high energy X-ray beam with almost consistent intensity at various angles and having a very small focus size in the thickness direction of the fan plane of the X-ray beam. This apparatus for generating a planar fan-shaped high energy X-ray beam having uniform intensity may be adopted in regular X-ray fluoroscopy imaging systems, which is beneficial to improve imaging consistency at various angles and increase the resolution in the moving direction of the object and thus improve image quality.

FIG. 8 (B) shows arranging two collimators on the same side of the electron beam E to draw out two planar fan-shaped high energy X-ray beams, each having relatively uniform intensity distribution in its respective plane, wherein these two X-ray beams have different draw-out angles. The collimator 202a forms an angle θ1 with the electron beam E, and the collimator 202b forms an angle θ2 with the electron beam E, θ1≠θ2. This apparatus for generating two planar fan-shaped high energy X-ray beams having uniform intensity and different angles of views on the same side may be adopted in double-angles-of-views X-ray fluoroscopy imaging systems (a fluoroscopy imaging technology of obtaining 3D information using double-angles-of-views X-ray fluoroscopy imaging systems has been disclosed in several patents of the Nuctech Company Limited), and may increase inspection speed and form a radiographic image with 3D information. Through the use of the apparatus of the present invention, image quality of the system may be improved.

FIG. 8 (C) shows an example of arranging two collimators in a direction forming an angle less than 90° with the electron beam E and in a direction forming an angle larger than 90° with the electron beam E, respectively, to draw out two planar fan-shaped high energy X-ray beams having relatively uniform intensity distribution in their respective planes, wherein the two X-ray beams have a significant energy difference therebetween. The collimator 202a forms an angle θ1<90° with the electron beam E and draw out an X-ray beam having higher integrable energy; and the collimator 202b forms an angle θ2>90° with the electron beam E and draw out a X-ray beam having lower integrable energy. This apparatus for generating two planar fan-shaped high energy X-ray beams having uniform intensity and different energy on the same side may be used in double-energy X-ray fluoroscopy imaging systems (advantages and applications of the double-energy technology have been disclosed in several patents of the Nuctech Company Limited), capable of obtaining a shape and structure image of an object under inspection and recognizing its component material. Thus, a double-energy inspection effect may be realized using a conventional single-energy electron accelerator as a radiation source. Compared with existing schemes in which a double-energy electron accelerator must be used as a radiation source, system complexity is lowered and cost is saved.

FIG. 8 (D) shows an example of arranging, respectively, two collimators symmetrically on both sides of a plane perpendicular to the electron beam E to draw out two planar fan-shaped high energy X-ray beams having relatively uniform intensity distribution in their respective planes, wherein the two X-ray beams have a significant energy difference therebetween and form symmetrical angles of views with respect to the object under inspection. The collimator 202a forms an angle θ1<90° with the electron beam E and draw out a X-ray beam having higher integrable energy; and the collimator 202b forms an angle θ2>90° with the electron beam E and draw out a X-ray beam having lower integrable energy, θ1+θ2=180°. This apparatus for generating two planar fan-shaped high energy X-ray beams symmetrical with respect to the 90° direction having uniform intensity and different energy on the same side may be used in double-energy/double-angles-of-views X-ray fluoroscopy imaging systems to realize X-ray fluoroscopy imaging system capable of achieving multiple-layer imaging and material reorganization using one conventional high energy single energy electron accelerator as a radiation source.

FIG. 8 (E) shows an example of arranging two collimators on both sides of the electron beam E and symmetrically with respect to the electron beam E to draw out two planar fan-shaped high energy X-ray beams having a relatively uniform intensity distribution in their respective planes. These two X-ray beams have the same characters, such as spectrum characters, focus size, radiation intensity, angle distribution and so on. The collimator 202a forms a "positive" angle θ1 with the electron beam E, the collimator 202b forms a "negative" angle θ2 with the electron beam E, and θ1+θ2=0. This apparatus for generating two X-ray beams with identical characters on two sides may be used in a double-channel X-ray fluoroscopy imaging system, so that the processing capability of the X-ray fluoroscopy imaging system using an electron accelerator as the radiation source may be doubled, while the system's image quality is improved.

FIG. 8 (F) shows an example of arranging multiple collimators on both sides of the electron beam E to draw out multiple planar fan-shaped high energy X-ray beams having a relatively uniform intensity distribution in their respective planes. These multiple X-ray beams have a variety of characters, respectively, such as identical intensity distribution in their planes, or low energy, or high energy, or small focus size, or different angles of views. The collimator 202a forms angle θ1 with the electron beam E, the collimator 202b forms angle θ2 with the electron beam E, the collimator 202c forms angle θ3 with the electron beam E, and the collimator 202d forms angle θ4 with the electron beam E, wherein there is some relationship between θ1, θ2, θ3, θ4, or they are independent with each other. The number of collimators may be also more than four. This apparatus for generating multiple X-ray beams on two sides may be used in an X-ray fluoroscopy imaging system having functions in a combination of double-energy/double-angles-of-views/double-channel.

Note that, as to the multiple collimators of the present invention, their gaps for defining the shapes of the fan shaped X-ray beams may have the same or different thickness.

Note that, as to the multiple collimators of the present invention, their fan opening angles for defining the shapes of the fan shaped X-ray beams may be the same or different.

Note that, as to the multiple collimators of the present invention, the central lines of the fan shaped X-ray beams may be located on the same plane, such as the "X-Y" horizontal plane, or on different planes.

Note that, as to the multiple collimators of the present invention, they may be located on one side of the electron beam E, or on both sides of the electron beam E, respectively.

Note that, as to the multiple collimators of the present invention, their positions are symmetrical with respect to a plane passing through the target point and perpendicular to the electron beam E.

Note that, as to the multiple collimators of the present invention, the positions thereof are symmetrical with respect to the electron beam E.

Note that, in the above description of the present invention, the electron accelerator 1 may produce a high energy electron beam E of above 2 MeV in a single amount of energy, or may be a double/multiple energy electron accelerator generating different energy quantities at different timings. In this case, in addition to obtaining different energy quantities in different spaces, it is also possible to obtain X-ray beams having different energy quantities at different timings in the present invention, and in general, to obtain X-ray beams having multiple energy quantities due to spatial and temporal difference.

Embodiments (System Construction)

As shown in FIG. 1, FIG. 3, FIG. 5, FIG. 7, FIG. 8, the apparatus for generating a planar fan shaped high energy X-ray beam having uniform intensity comprises a high energy electron accelerator 1 and a shielding and collimating device 2. The electron accelerator 1 comprises electron emission unit 101, electron acceleration unit 102, electron drift segment 104 and target 103. The electron emission unit 101 is mounted at the front end of the electron acceleration unit 102. The electron drift segment 104 is mounted on the back end of the electron acceleration unit 102 to connect the electron acceleration unit 102 with the target 103. The electron accelerator 1 with 9 MeV energy may produce an X-ray beam having a maximum intensity of 3000 Rad/m·min. The shielding and collimating device 2 comprises shielding structure 201 and multiple collimators 202a, 202b, 202c, 202d. The shielding structure 201 surrounds the target 103 and is made of lead. The shielding structure 201 is thick enough in various directions, such that the intensity of X-rays may be attenuated by an order of above $10^3$ in various directions. The shielding structure 201 is formed by multiple blocks to facilitate fabrication and assembly thereof. Collimators 202a, 202b, 202c, 202d are planar fan gaps arranged in different positions in the shielding structure 201. All of the planes where the fan gaps locate pass through the target point o and are perpendicular to the pager surface shown in FIG. 8. All of these fan gaps has a thickness of 2 mm, and take the center point of the fan as the target point o. All those fans have their center lines on the "X-Y" horizontal plane and have a fan opening angle of 90°. The collimator 202a forms an angle θ1 of 45° with the electron beam E, the collimator 202b forms an angle θ2 of 135° with the electron beam E, the collimator 202c forms an angle θ3 of −60° with the electron beam E, and the collimator 202d forms an angle θ2 of −90° with the electron beam E.

(Operation Principle)

The electron accelerator 1 is under the actuation of an auxiliary system (for example, a power supply and a control system), and the electron emission unit 101 produces an electron beam E, which enters into the electron acceleration unit 102 and is accelerated to a high energy electron beam E, for example an electron beam E of 9 MeV. The high energy electron beam E passes through the electron drift segment 104 and bombards the target 103 to produce X-rays having an intensity distribution over various directions in space as shown in FIG. 3. Most of the X-rays are shielded and absorbed by the shielding structure 201. Four planar fan-shaped X-ray beams having different characters are drawn out from collimators 202a, 202b, 202c, 202d, respectively. The planar fan-shaped X-ray beam drawn out from collimator 202a has a higher energy quantity, a larger central radiation intensity, and larger variations in X-ray intensity in the range of the fan opening angle; the planar fan-shaped X-ray beam drawn out from collimator 202b has a smaller energy quantity, a lower central radiation intensity, and smaller variations in X-ray intensity in the range of the fan opening angle; the planar fan-shaped X-ray beam drawn out from collimator 202c has a medium energy quantity, a moderate central radiation intensity, and smaller variations in X-ray intensity in the range of the fan opening angle; and the planar fan-shaped X-ray beam drawn out from collimator 202d has a smaller energy quantity, a lower central radiation intensity, and no variation in X-ray intensity in the range of the fan opening angle.

The apparatus for generating a planar fan-shaped high energy X-ray beam having uniform intensity of the present invention may be used in an X-ray fluoroscopy imaging system. Two inspection channels may be arranged on upper and lower sides (with respect to the description of FIG. 8(F)) in parallel with the electron beam E. In the upper channel, collimators 202a and 202b provide two X-ray beams having different angles of views and having significant variations in X-ray energy and intensity to achieve the effect of double-energy inspection; and in the lower channel, collimators 202c and 202d provide two X-ray beams having different angles of views and without significant variations in X-ray energy and intensity to achieve the effect of double-angles-of-views inspection. Applying the present invention in an X-ray fluoroscopy imaging system and using a low cost conventional high energy electron accelerator as an X-ray source, multiple functions such as improved image quality, increased inspection speed, increased layering information of images, and increased capability of recognizing imaged materials are achieved.

ADVANTAGE EFFECTS

The present invention mainly provides an apparatus for generating a planar fan-shaped high energy X-ray beam having uniform intensity. Through arranging the collimator in a direction forming a lager angle with the direction of the electron beam shooting the target, a X-ray beam may be obtained with better quality, such as (1) more uniform intensity of X-rays in various directions within a fan area on a plane; (2) the smaller energy dispersion of X-rays within the fan area on the plane; and (3) a smaller size projection point of X-rays target point on the plane. These three properties may improve the image quality of the X-ray fluoroscopy imaging system. Due to better uniformity of X-rays, X-rays may be drawn out at a large angle to increase X-ray coverage within a closer distance. Multiple collimators are arranged in the shielding and collimating device, with different angle and position relationships, so as to realize: (1) obtaining multi-angles-of-views images from multiple angles of views; (2) obtaining double-energy effect by means of generating X-ray beams with different energy quantities from different collimators, so as to determine materials of objects under inspection; (3) implementing a double-channel inspection system using one accelerator to improve the inspection speed of the X-ray fluoroscopy imaging system and its cost performance; and a combination thereof to form an X-ray fluoroscopy imaging system in different combinations of double channel/high energy/multiple angles of views.

As described above, embodiments of the present invention have been described as such. However, the present invention is not limited thereto and various variations may be made to them. It should be understood that all of these variations that are made under the technical concept of the present invention shall be encompassed in the scope of the present invention.

What is claimed is:

1. An X-ray generating apparatus, characterized in comprising:
    an electron accelerator including an electron acceleration unit, an electron emission unit, and a target; and
    a shielding and collimating device, including a shielding structure and multiple collimators arranged in the shielding structure,
    wherein the target is surrounded by the shielding structure, the collimators are thin gaps extending from the target to an exterior surface of the shielding structure and having an axis transverse an electron beam shooting the target, and the planes where the collimators locate form angles from 30 degrees to 150 degrees with the electron beam shooting the target, to draw out planar beams, each having uniform intensity distribution in its respective plane, wherein the planar beams have energy difference therebetween;

the electron accelerator further comprises an electron drift segment connected between the electron acceleration unit and the target, the electron drift segment is a small diameter conduit, wherein the small diameter conduit has an inner diameter larger than the diameter of the electron beam and an outer diameter less than the outer diameter of the electron acceleration unit.

2. The X-ray generating apparatus according to claim 1, characterized in that:
the electron accelerator has energy of above 2 MeV.

3. The X-ray generating apparatus according to claim 1, characterized in that:
each of the collimator is a planar fan-shaped gap arranged in the shielding structure.

4. The X-ray generating apparatus according to claim 1, characterized in that:
the shielding structure is made from a material that is able to block and absorb most of undesired X-rays.

5. The X-ray generating apparatus according to claim 1, characterized in that:
the target is a planer structure, a spherical surface structure, or other curved surface structure.

6. The X-ray generating apparatus according to claim 1, characterized in that:
the positions of the multiple collimators are symmetrical with respect to a plane passing the target point and perpendicular to the electron beam.

7. An X-ray fluoroscopy imaging system, characterized in comprising the X-ray generating apparatus according to claim 1.

8. The X-ray generating apparatus according to claim 1, characterized in that: the shielding and collimating device consists of two collimators on the same side of said electron beam to draw out two planar fan-shaped beams, each having uniform intensity distribution in its respective plane, wherein the two planar fan-shaped beams have different draw-out angles.

9. The X-ray generating apparatus according to claim 1, characterized in that: the shielding and collimating device consists of two collimators in a direction forming an angle less than 90° with said electron beam and in a direction forming an angle larger than 90° with said electron beam, to draw out two planar fan-shaped beams, each having uniform intensity distribution in its respective plane, wherein the two planar fan-shaped beams have energy difference therebetween.

* * * * *